United States Patent [19]

Huber

[11] Patent Number: Plant 7,251

[45] Date of Patent: Jun. 19, 1990

[54] THORNLESS BLACKBERRY NAMED "PER CAN"

[75] Inventor: Tony Huber, Laval, Canada

[73] Assignee: W. H. Perron et Cie. Ltee., Quebec, Canada

[21] Appl. No.: 178,334

[22] Filed: Apr. 6, 1988

[51] Int. Cl.[5] ..... A01H 5/00

[52] U.S. Cl. ..... Plt./46

[58] Field of Search ..... Plt./46

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Nordic-type blackberry variety named "Per Can" combines the characteristics of cold-hardiness, thornless branches and stems, adaptability to various soil conditions, vigor and strength, absence of suckering, and ease of propagation by tissue culturing. Per Can yields berries characterized by an excellent taste (slightly acid, slightly sugary), a very fresh appearance and appealing texture, with a real blackberry aroma and no noticeable aftertaste.

5 Drawing Sheets

BACKGROUND OF THE INVENTION

The present invention relates to a new and distinctive cultivar of blackberry plant named Per Can. This cultivar belongs to the genus Rubus, which also includes a number of soft fruits, such as raspberries, loganberries, gooseberries, currants and achenes, cultivated for culinary purposes. The typifying characteristics of these soft fruits are well-known from various publications, including "Soft Fruits," 2 THE BIOCHEMISTRY OF FRUITS AND THEIR PRODUCTS, pages 375–377 (1971).

Species of blackberry plants vary in color, size, shape, acidity, and other commercially important and botanically significant characteristics. For example, *R. allegheniesis* has many small drupelets, while *R. frondosus* is more rounded and has comparatively fewer. Blackberries frequently bear flowers and fruit simultaneously, and fruit tends to ripen randomly on the canes.

Origin of the Variety

The new cultivar of the present invention was developed by me in Laval, Canada, as a selection derived from *Rubus canadensis;* the cultivar is thus not a hybrid. The wild growing Canadian parent was collected on the Appalachian plateau, in southern Quebec. This parent grows in thornless or nearly thornless populations.

In developing Per Can, I selected six completely thornless specimens of *R. canadensis* from the wild population. After two years of propagation, over 50% of the best seedlings were totally thornless. Three additional years of propagation through very cold winters resulted in a single thornless plant have superior winter hardiness. It produced normal fruits during mid- to late-summer (July-September) in southern Quebec.

This new cultivar must be asexually reproduced by tip-cutting or tissue culture. Both methods give good results, but commercial propagation is very much faster by tissue culture. The absence in this cultivar of suckers precludes propagation by root cuttings. The "Per Can" thornless blackberry has been asexually reproduced. For commercial requirements, the propagation to produce a stable variety has been made by tissue culture at Congdon & Weller Wholesale Nursery Inc., in the state of New York.

DESCRIPTION OF THE PHOTOGRAPHS

The accompanying photographs illustrate the color and other features of the new cultivar, showing it in various stages of fruit maturation.

Sheet 1 is a view of a blackberry bush of the Per Can variety, showing the fruit in different stages of maturity.

Sheet 2 is a close-up view of a cane of the variety, also showing the fruit in different stages of maturity.

Sheet 3 shows the variety with unripened fruit and, in addition, provides a good view of the leaves of the plant.

Sheet 4 is a closeup view of unripened fruit of the variety.

Sheet 5 is a view of the mature fruit of the variety.

DESCRIPTION OF THE VARIETY

The Nordic-type cultivar of the present invention exhibits excellent resistance to temperatures as low as −40° F., and was the most cold-hardy among many others tested. Also, it is thornless, which obviously makes cultivation and harvesting easier and enhances it commercial potential. Per Can adapts well to various soils, but prefers neutral (approximately pH 6.8) to acid soil.

While both tip-cutting and tissue culturing are conventional propagating techniques for the genus Rubus, tissue culturing is the preferred mode of reproducing Per Can because virus-free propagation is thereby assured. Tissue culturing thus utilizes artificial nutrient media under aseptic (pathogen-free) conditions in controlled laboratory environments. See Murashige, "Plant Propagation Through Tissue Cultures," *Ann. Rev. Plant Physiol.* 25: 135–66 (1974), the contents of which are hereby incorporated by reference.

In general terms, tissue culture is divided into four stages of development. The first stage (stage 1) entails establishing a sterile culture of a portion (explant) of the stock plant. During stage 2 there is a stimulation of multiple shoot development, which usually involves transferring cultured material to a medium with containing levels of the plant hormone cytokinin. Stage 3 involves preparing the cultured material for removal from culture, a process that typically entails exposing the material to increased auxin levels to initiate roots on shoots which were multiplied in stage 2. Finally, cloned plants are adapted to greenhouse conditions during stage 4, in the course of which there is always a gradual reduction of humidity until the plants are hardened off.

With regard to the Per Can cultivar, stage 4 usually includes rooting, that is, the variety of the present invention can be rooted directly in stage 4; accordingly, stage 3 is optional. The specific details of Rubus propagation are otherwise conventional, as disclosed, for example, by Anderson, *In Vitro* 15 (3): 177 (1979), and *Acta Hort.* 112: 13–20 (1980); by Pyott and Converse, *Hort. Sci.* 16(3): 308–309 (1981); and by Snir, *Scienta Hort.* 14: 139–143 (1981), the respective contents of which documents are hereby incorporated by reference.

Prior to maturity, the fruit of the Per Can variety has a reddish color. When fully ripe, the fruit has a dark black color identified with color 202A of the Royal Horticultural Society (RHS) Colour Chart. The leaves, when fully developed, have a yellow/green color, corresponding to color 147A of the RHS Chart, and are simple, first leaves are three-lobed, further appearing leaves are five-lobed. Leaves are slightly pubescent on both sides. During the maturing process, the leaves have a yellowish periphery.

The plant canes are two-toned. More specifically, the portion of the canes are two-toned. More specifically, the portion of the cane exposed to the sun has a grey/-purple color corresponding to RHS color 183C. The shaded portion of the cane is yellow/green, with a color corresponding to RHS color 144B. (The color evaluations described herein were made in St. Eustache, Quebec, Canada, on the morning of Aug. 24, 1987, at 9:30 a.m. Viewing was effected in direct sunlight, under dry, cool conditions, when the temperature was about 60° F.).

As shown in the table below, chemical analyses reveal substantial differences between Per Can and typical cultivated blackberry varieties. These analyses involve comparisons of pH, Brix value (percent of soluble solids), acidity (percent of citric acid found in the berries) and humidity (percent of moisture).

TABLE

| | pH | Brix Value | Acidity (%) Citric Acid | Humidity (%) |
|---|---|---|---|---|
| Per Can Variety | 3.36 | 9.1 | 0.84 | 87.68 |
| Typical Cultivated Variety* | 3.0 | 8.9 | trace amounts | 84.8 |

*Values derived from "Soft Fruits," loc. cit., at Tables II and V.

One of the major soluble components of blackberries and other soft fruit is its sugar. The sugar-to-acid ratio is important in determining flavor and commercial acceptability. Sensory evaluations indicate that Per Can yields berries characterized by an excellent taste (slightly acid, slightly sugary). There is no noticeable aftertaste, and the fruit has real blackberry aroma. It also has a very fresh appearance and appealing texture.

Per Can is vigorous and strong, not suckering. Canes are biennial, trailing, and may reach a length of about 12 feet (350 cm) in good and heavy garden soil. Growth is slower and less vigorous in sandy soil, with canes reaching about 5 feet (150 cm). Typically, the variety needs trellising to control growth. The variety produces drupelets of about 6 millimeters in diameter. Seeds of the variety have a flattened kidney shape, and average 4 millimeters in length, 3 millimeters in width and 1.5 millimeters in thickness.

The largest leaves of the variety are basal, averaging 19 to 32 centimeters in length. Leaf size decreases at higher positions on the stem, averaging 20 to 22 centimeters in length at the top of the stem. Leaf sizes are measured from the base of the petiole.

Firmness of fruit of the variety (Newtons) has been measured at 43.0±3.8. Juiciness has been measured at 80.0%±3%.

Inflorescenses of Per Can are glandless, white and produced in clusters of more than 30 from June until September in northern temperate climates. Fruits ripen from mid-July to late October in this zone. The berries are round and slightly conical (length: about 30 mm; diameter: about 20 mm). The weight of one berry ranges from about 4.5 grams to about 8.7 grams with the average weight of one berry being about 4.5 grams.

The variety should be planted in sunny and dry locations on trellises or wire supports, spaced about 10 inches apart. Per Can is useful for home gardens, as well as "pick-your-own" and contract growing. After harvesting, all canes that produced fruit, i.e., those that are two years old, should be pruned. In addition, (cut-out) one year-old canes should be thinned and tied to trellises or wires.

In colder zones, the canes should be laid on the ground and, if necessary, protected with mulch. Canes should be tied to wires the following growing season, and the plants should not be fertilized after the beginning of August.

I claim:

1. A new and distinct cultivar of *Rubus canadensis,* named Per Can, as herein shown and described, characterized particularly as to uniqueness by the combined characteristics of cold-hardiness, thornless branches and stems, adaptability to various soil conditions, vigor and strength, absence of suckering, and ease of propagation by tissue culturing.

* * * * *

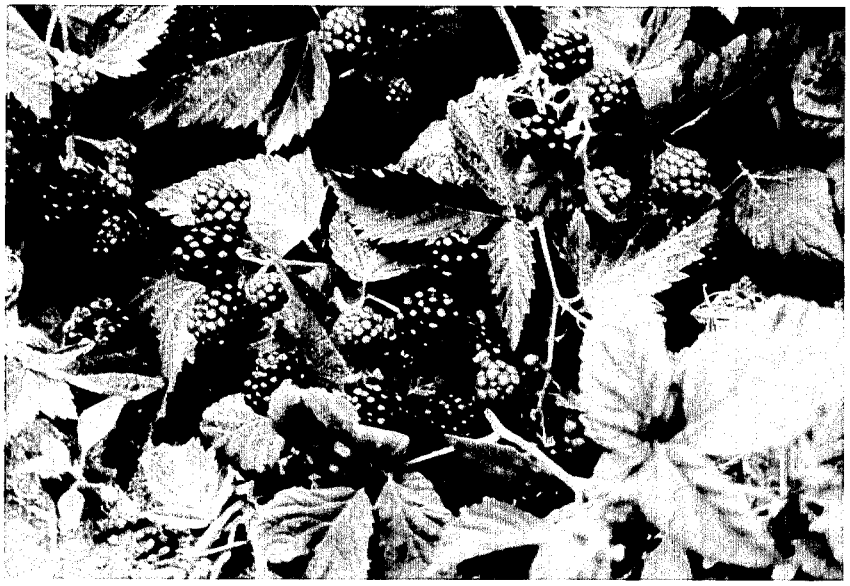

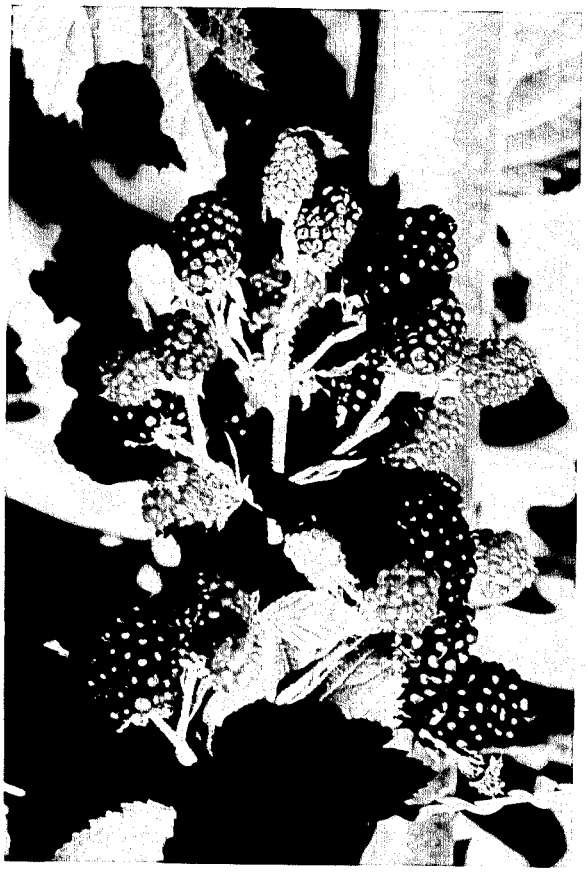

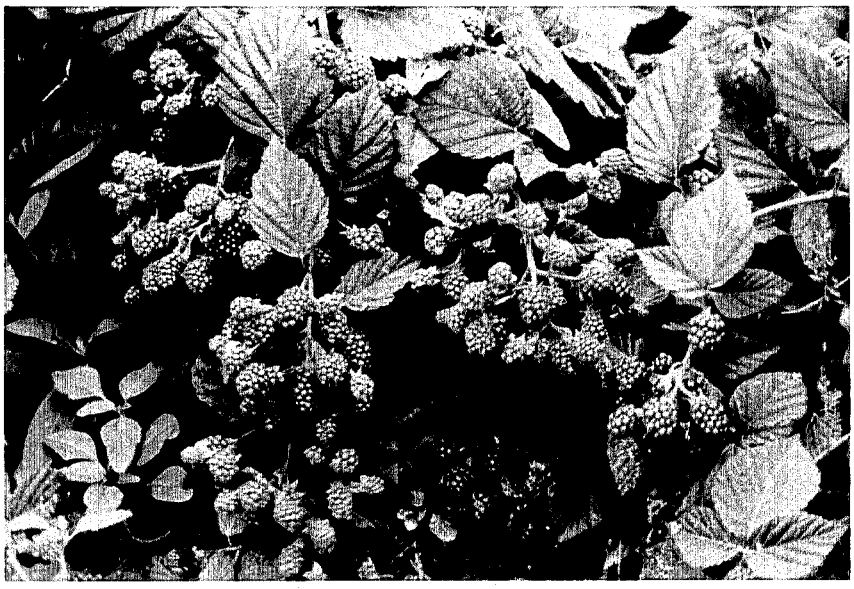

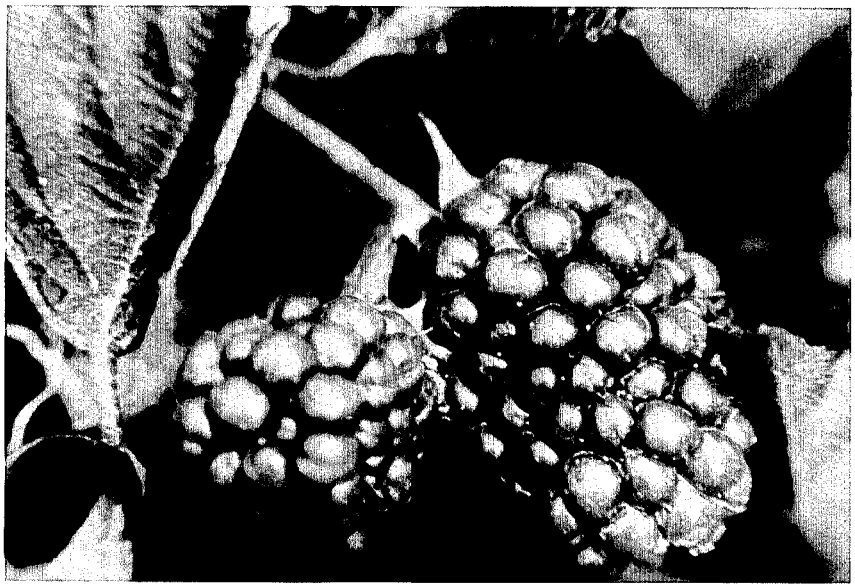

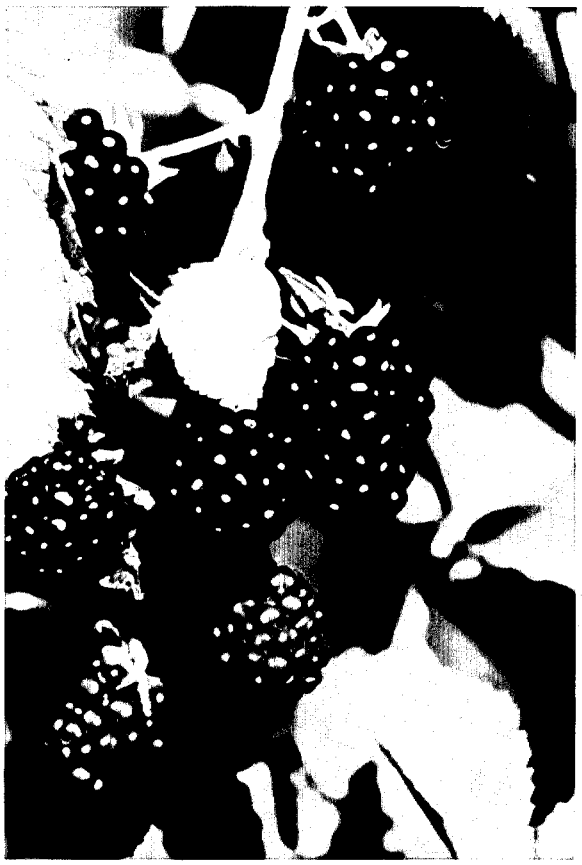

UNITED STATES PATENT AND TRADEMARK OFFICE

CERTIFICATE OF CORRECTION

PATENT NO. : Plant Patent No. 7,251

DATED : June 19, 1990

INVENTOR(S) : Tony Huber

It is certified that error appears in the above-identified patent and that said Letters Patent is hereby corrected as shown below:

In the Abstract, line 3, change "branches and stems" to -- canes --.

Column 2, line 22, change "it" to -- its --.

Column 4, line 16, change "32" to -- 23 --.

Column 4, line 18, change "length" to -- width --.

Column 4, line 29, change "4.5" to -- 3.3 --.

Column 4, line 36, after "pruned" insert -- (cut-out) --.

Claim 1, line 4, change "branches" to -- canes --.

Signed and Sealed this

Eighteenth Day of August, 1992

*Attest:*

*Attesting Officer*

DOUGLAS B. COMER

*Acting Commissioner of Patents and Trademarks*